ized Fluropolyure-
United States Patent [19]
Kim et al.

[11] Patent Number: 5,242,995
[45] Date of Patent: Sep. 7, 1993

[54] PERFLUOROCARBON-GRAFTED POLYURETHANE WITH IMPROVED BLOOD COMPATIBILITY AND PROCESS FOR THEIR PREPARATION

[75] Inventors: Young H. Kim; Dong K. Han, both of Seoul, Rep. of Korea

[73] Assignee: Korea Institute of Science and Technology, Seoul, Rep. of Korea

[21] Appl. No.: 766,065

[22] Filed: Sep. 27, 1991

[30] Foreign Application Priority Data

Jan. 7, 1991 [KR] Rep. of Korea .................. 91-95

[51] Int. Cl.$^5$ .................. C08F 283/04; C08F 8/00
[52] U.S. Cl. .................. 525/453; 525/454; 525/457; 528/488; 528/489; 424/423; 623/1; 623/2; 623/3
[58] Field of Search .................. 525/453, 454, 457; 528/488, 489; 424/423; 623/1, 2, 3

[56] References Cited

U.S. PATENT DOCUMENTS

| | | | |
|---|---|---|---|
| 3,255,131 | 6/1966 | Ahlbrecht et al. | 525/453 |
| 3,852,222 | 12/1974 | Field et al. | 525/453 |
| 4,728,542 | 3/1988 | Nachtkamp et al. | 525/453 |
| 4,739,013 | 4/1988 | Pinchuk | 525/453 |
| 4,883,699 | 11/1989 | Aniuk et al. | 525/453 |
| 4,923,929 | 5/1990 | Ohwada et al. | 525/454 |
| 5,017,664 | 5/1991 | Grasel et al. | 604/266 |
| 5,034,461 | 7/1991 | Lai et al. | 525/453 |
| 5,057,377 | 10/1991 | Karydas et al. | 525/453 |
| 5,061,770 | 10/1991 | Tamaru et al. | 525/454 |
| 5,087,687 | 2/1992 | Fock et al. | 528/45 |

OTHER PUBLICATIONS

Teruo Takakura et al., "Segmented Fluropolyurethanes," IUPAC Intern'l Symposium, Jun. 26-28, Seoul, Korea, pp. 314-315 (1989).
"Waterproofing and Water/Oil Repellency" in Encyclopedia of Chemical Technology, vol. 24, John Wiley & Sons, New York, pp. 442-465 (1984).
Yoshihiro Ito et al. "Synthesis, Blood Compatibility and Gas Permeability of Copolypeptides containing Fluoroalkyl Side Groups," Int. J. Biol. Macromol., vol. 10, pp. 201-208 (1988).
T. Takakura et al. "Fluorinated Polyurethaneureas with Antithrombogenic Properties," 2nd SPSJ International Polymer Conference, p. 46. (1986).
Richard J. Zdrahala et al. "Hemocompatibility of Polyether-Polyurethanes, Effect of Fluorine-containing Intermediates," The Third World Biomaterials Congress, Apr. 21-25, Kyoto, Japan, p. 425 (1988).
B. D. Rather, "Surface Analysis of Biomedical Materials by ESCA and SIMS," Polymers in Medicine III, pp. 87-98 (1988).
Yoshihiro Ito et al. "Design and Synthesis of Blood--compatible Polyurethane Derivatives," Artificial Heart 2, Tokyo, Japan, Aug. 13-14, pp. 35-41 (1987).

*Primary Examiner*—John Kight, III
*Assistant Examiner*—Rabon Sergent
*Attorney, Agent, or Firm*—Oblon, Spivak, McClelland, Maier & Neustadt

[57] ABSTRACT

Novel modified polymeric materials are provided. The polymeric materials according to the invention are prepared by grafting a fluorine-containing compound onto a polyurethane polymeric substrate. The polymeric materials show superior blood compatibility in the in vitro and ex vivo tests, attributing to hydrophobic property, inertness and water-repelling property intrinsic to the grafted fluorine containing compounds.

The polymeric materials according to the invention are useful as the materials for the artificial, circulatory, internal organ systems to be contacted with blood, such as artificial hearts, artificial blood vessels, artificial heart valves, artificial blood oxygenators, and artificial kidneys, or for the medical devices/instruments to be inserted into the blood vessels, such as vein catheters, artery catheters and intra-aortic balloon pumps.

4 Claims, No Drawings

PERFLUOROCARBON-GRAFTED POLYURETHANE WITH IMPROVED BLOOD COMPATIBILITY AND PROCESS FOR THEIR PREPARATION

BACKGROUND OF THE INVENTION 1. Field of the Invention

The present invention relates to a novel modified polymeric material, more particularly, perfluorocarbon-grafted polyurethanes having superior blood compatibility, and a process for their preparation. 2. Description of the Prior Art In biomaterials to be contacted with blood, hydrophobic surfaces thereof exhibit inertness and lower interaction with aqueous solutions due to low surface free energy. In addition, biomaterials hardly absorb water so that their mechanical characteristics can be maintained in the entirety thereof.

It has been known that fluorine-containing compounds provide typically hydrophobic surfaces, the surface tension of which is lower than that of water, oil and other solvents. For these characteristics, fluorine-containing compounds have been employed in the technical field of surface treatment of fibers, such as waterproofing treatment, oil/water repelling treatment, and others [M. Hayek, "Encyclopedia of Chem. Tech." Vol. 24, p.442 (1984)]. A representative copolymer is the one of acrylic or methacrylic esters containing fluoroalkyl chains such as Scotchgard (commercially available from The 3M Company) and Zepel (commercially available from E. I. Du Pont De Nemours and Company). The maximum water-repelling property can be obtained when the number of carbon atoms constituting the fluoroalkyl chains is 6-8. It is believed that this water repelling property attributes to the exposed $CF_3$ groups present in the fluoroalkyl chains which outwardly extend from the surfaces of the copolymers.

Particularly, fluorocarbon polymers have been used as medical materials, such as artificial blood vessels. The representative example includes an expanded polytetrafluoroethylene which is being sold under the tradename "Gore-Tex."

A number of studies have heretofore been made on polymeric materials having a hydrophobic surface by utilizing fluorine-containing compounds in order to enhance antithrombogenicity.

For example, Ito et al. reported that in L-glutamate copolymers containing a fluoroalkyl group, blood coagulation is decreased and interaction of the surface of the copolymers with blood components, including plasma proteins, platelets, and blood coagulation factors, is considerably suppressed, with the increase in the fluorine content of the copolymers [*Int. J. Biol, Macromol.*, 10, pp 201-208 (1988)].

On the other hand, a number of studies, in which fluorine-containing compounds are used in place of conventional diisocyanates, polyols or chain extenders, have been made in attempt to improve further blood compatibility of the polyurethanes.

For example, Takakura, et al. have used a fluorinated diisocyanate in place of diphenylmethane diisocyanate (MDI) [2nd SPSJ Int. Polym. Conf., p.46 (1986)]. Zdrahala, et al. have used fluorinated glycols having a molecular weight of 1,600 in place of polytetramethylene glycol (PTMG) [3rd World Biomat. Congress, p.425 (1988)]. Also, Ratner has employed a fluorinated chain extender for the synthesis of polyurethane [*Polymer in Medicine III*, p.87 (1988)]. Ito, et al. [*Artificial Heart II*, p.35 (1987)] and Takakura, et al. [IUPAC Int. Symp. p.314 (1989)] have used fluorine-containing compounds in synthesizing polyurethanes.

The fluorine-containing polyurethynes synthesized according to these conventional methods exhibit a relatively increased blood compatibility and suppressed interaction with blood attributing to the hydrophobic surfaces of the polyurethanes and the strong electronegative effect of the fluorine atom. However, these conventional methods suffer from the defects that the mechanical properties of polyurethanes deteriorate during the synthesis of fluorinated polyurethanes. Moreover, the blood compatibility of the fluorine-containing polyurethanes thus obtained is insufficient to use them as biomaterials.

SUMMARY OF THE INVENTION

The object of the invention is to provide novel, modified polyurethanes having significantly improved blood compatibility.

Another object of the invention is to provide a process for increasing the blood compatibility of polyurethanes without reducing original mechanical properties of polyurethane itself.

These and other objects of the invention will become apparent through reading the remainder of the specification.

DETAILED DESCRIPTION OF THE INVENTION

The modified polyurethanes according to the invention are prepared by grafting a fluorine-containing compound having hydrophobicity, inertness, and a water repelling property to polyurethane polymeric substrates.

The process for preparing the modified polyurethanes according to the invention is different from the conventional processes described above in which various kinds of fluorine-containing compounds participate in the synthesis of polyurethanes.

The process according to the invention employs commercially available polyurethanes as polymeric substrates for grafting the fluorine-containing compounds. More specifically, the process according to the invention comprises first reacting commercially available polyurethane with diisocyanate to introduce reactive functional groups thereinto, and then grafting a derivative of fluorine-containing compounds onto the reactive functional groups thus introduced. Alternatively, the modified polyurethanes according to the invention can be prepared by reacting a polyurethane polymeric substrate with a halogen derivative of fluorine-containing compounds after producing an urethane ion by the action of strong base.

The polymeric substrates employed in the present invention include polyurethanes having urethane groups containing a displaceable hydrogen atom. The activity of hydrogen atoms present in the urethane groups is not so high, but substitution may give to rise depending on the reaction conditions. Thus, the hydrogen atoms can either react directly with a strong nucleophilic compound such as diisocyanate, or undergo a substitution reaction with a halogen derivative after the formation of an urethane ion by the action of a strong base.

The present invention has so far been described mainly with respect to the use of polyurethane as the polymeric substrate. However, it will be apparent to those skilled in the art that any copolymers containing urethane groups, such as fluorinated polyurethane or polyurethane-silicone copolymers, can also be employed in the present application as the polymeric substrates.

The term "fluorine-containing compounds" or "derivatives of fluorine-containing compounds" used in the present invention means a saturated $C_1$-$C_{12}$ aliphatic perfluorocarbon having a hydroxyl or carboxyl group or an halogen atom at one terminal and a —$CF_3$ group at the opposite terminal.

The hydrophobicity of polymer surfaces can be varied by changing the chain length of the fluorine-containing compounds used. The fluorine-containing compounds have hydrophobicity, inertness and water repelling properties, as well as very low surface free energy as described above. Attributing to these properties, the polymeric substrates having grafted fluorine-containing compounds show a low interaction with blood components, yielding superior blood compatibility. Particularly, it is considered that the superior antithrombogenicity of the modified polyurethanes is a result of their surface structure; the entire chains of the grafted fluorocarbon straightly extend from the surfaces of the polymeric substrates in the outward direction and thereby the —$CF_3$ terminal groups are exposed to the exterior of the polyurethane substrates.

The processes for introducing fluorine-containing compounds into the polyurethane polymeric substrates according to the invention will be described below with reference to a detailed illustrative reaction scheme thereof.

The first process comprises a reaction in which diisocyanates are treated with a polymeric substrate to introduce isocyanate functional groups thereinto, and a fluorine-containing compound is then bonded onto the isocyanate groups thus introduced.

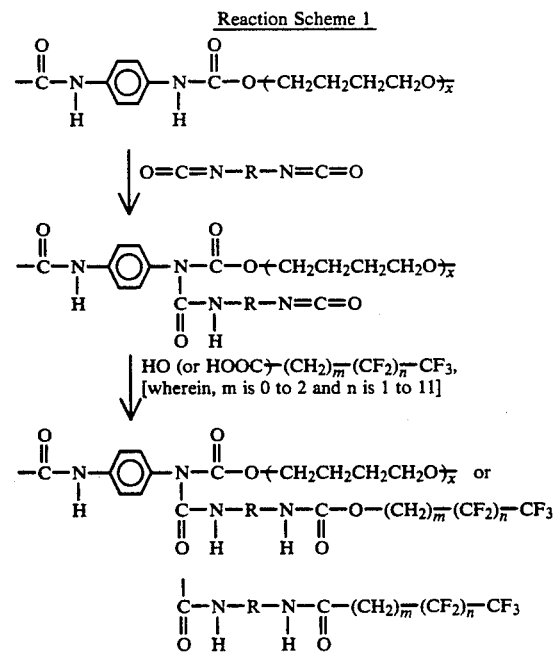

The diisocyanates useful in the invention include, for example, hexamethylene diisocyanate (HMDI), toluene diisocyante (TDI), diphenylmethane diisocynate (MDI), and the like. Organic stannous compounds or amines which are used as the catalyst for the polyurethane polymerization can also be employed in Reaction 1. This reaction proceeds under mild conditions and is thus advantageous in that the polymeric substrates are not deteriorated.

The second process comprises a reaction in which a polymeric substrate is treated with strong bases to form an urethane anion, and the urethane anion is then reacted with a fluorine-containing compound which further contains a halogen atom. Useful strong bases include, for example, sodium and potassium hydride, sodium and potassium ethoxide, sodium and potassium butylate, and methylmagnesium bromide. The reaction involved in the second process can be summarized in the following reaction scheme:

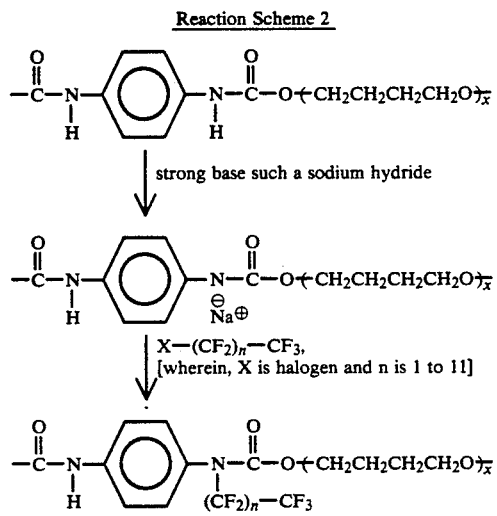

The processes for the preparation of modified polymers described above can be performed by a surface reaction on the polymeric substrate once molded. Alternatively, the polymeric materials can be modified in solution in a proper solvent, and the resultant polymeric solution is useful as a molding and coating material.

In the case of a surface reaction, it is essential to carry out the reaction in a medium in which the polymeric substrates are insoluble. It is preferred to use a medium having a lower swelling ability. Examples of useful solvents include tetrahydrofuran, dimethylacetamide, dimethylformamide, and the like. These solvents are properly selected depending on the types of reactions to be carried out, i.e., the surface reaction or solution reaction.

The modified polymers according to the invention may be used as the medical structural and coating materials, such as films, sheets, tubes, fibers or hollow fibers. Because the modified polymers according to the invention have superior blood compatibility, when they are used as the basic materials for the artificial, circulatory, internal organ systems to be contacted with blood, such as artificial hearts, artificial blood vessels, artificial heart valves, artificial blood oxygenaters and artificial kidneys, or for the medical devices or instruments to be inserted into blood vessels, such as vein catheters, artery catheters and intraaortic balloon pumps, the side effects which would be caused from blood coagulation can be significantly reduced.

Analysis for the contact angle of materials (hydrophobicity and hydrophilicity)

The hydrophobicity and hydrophilicity of the modified polymers according to the present invention are evaluated based on the dynamic contact angles determined by the Whilhelmy plate method [Smith, et al., J. Appl. Polym. Sci., 26, p.1269 (1982)]. This method is to determine the advancing contact angle and the receding contact angle by precisely measuring changes in the weight when the material is soaked in and taken out of water. The higher the advancing contact angle is, the greater the hydrophobicity of the material is, whereas the lower the receding contact angle, the greater the hydrophilicity of the materials.

Analysis for blood compatibility of materials (anti-thrombogenicity)

In vitro platelet adhesion test and ex vivo arterio-arterial shunt test using rabbits are used in order to evaluate the blood compatibility of materials.

The platelet adhesion test is to determine the amounts of platelets that adhere to each material. A sample material was dipped into a platelet rich plasma (PRP) at 37° C. for 3 hrs. The sample was removed and washed with a phosphate buffered saline (PBS) solution. After completing the washing, the sample was soaked into a 0.2% aqueous glutaraldehyde solution in a PBS buffer for 2 hrs. to fix the adhered platelets onto the surface of the sample. The sample so treated was dehydrated with an aqueous ethanol, freeze-dried, and then observed by a scanning electron microscopy.

Ex-vivo arterio-arterial shunt test is a method capable of simply and rapidly evaluating the blood compatibility of a material under animal experiment conditions using rabbits. This testing method is excellent in its reproducibility [C. Nojiri, et al., ASAIO J. 33, pp. 596-601 (1987)]. Both ends of a sample tube (inner diameter: 1.5 mm; outer diameter: 2.0 mm; length: 30 cm) are inserted into the right carotid artery of a rabbit to circulate blood in the form of a shunt. The blood is circulated at a controlled rate of 2.5 ml/min, and the time when the blood flow decreases to zero is defined as the occlusion time. A longer occlusion time represents better blood compatibility.

DESCRIPTION OF THE PREFERRED EMBODIMENT

The invention will be illustrated in greater detail by way of the following examples. The examples are presented for illustrative purpose only and should not be construed as limiting the invention which is properly delineated in the claims.

EXAMPLE 1

A polyurethane sheet of area 2 cm$^2$ and thickness 1 mm (Pellethane 2363-80A available from The Upjohn Company, Kalamazoo, Mich.) was refluxed in methanol at 60° C. for 24 hrs. to remove surface impurities, and then placed in toluene (120 ml). After adding hexamethylene diisocyanate (HMDI) (2 ml) and stannous octoate (0.5 ml), the resultant mixture was reacted at 20°-40° C. for 1-2 hrs., and then in turn sufficiently washed with toluene and anhydrous ether. The surface thus treated was observed by the attenuated total reflection-Fourier transform infrared spectroscopy (ATR-FTIR). As a result, free functional groups of the introduced isocyanates could be confirmed.

The resulting sheet was reacted with a mixture of toluene (40 ml) and perflurodecanoic acid (0.2 g) at 40° C. for 2 hrs. The sheet was removed, and then washed with toluene and acetone, in turn, to give a fluorinated polyurethane.

The advancing and the receding contact angles of the polyurethane sheet so modified were 110° and 54°, respectively. These angles indicate a significantly increased hydrophobicity as compared with the advancing contact angle (86°) and the receding contact angle (41°) of the untreated polyurethane sheets. The fluorinated polyurethane sheet thus modified shows a smaller amount of platelet adhesion and a lower degree of activation than the untreated ones.

The inner surface of the polyurethane tube (Royalthene R380 PNAT available from Uniroyal, Inc., inner diameter: 1.5 mm; outer diameter: 2.0 mm; length: 30 cm) was treated as done above and subjected to a rabbit arterio-arterial shunt test. The occlusion time was 130 min. This indicates a significantly increased compatibility as compared with the occlusion time of 50 min. for the untreated polyurethane.

Based on the above results, it could be confirmed that the blood compatibility of polyurethane has significantly improved through the modification according to the present invention.

EXAMPLE 2

The same procedures as described in Example were repeated, except that perfluorooctanol was used in place of perfluorodecanoic acid. The contact angles were significantly increased and the blood compatibility was equal to that in Example 1.

EXAMPLE 3

Polyurethane (5 g) was dissolved in dimethylacetamide (95 ml). Hexamethylene diisocyanate (5.5 ml) was added to the resulting solution to undergo a bulk reaction at 40°-50° C. for 1-5 days. After precipitation with anhydrous ether and subsequent separation, the product (3 g) was dissolved in dimethylacetamide (97 ml) again. Perfluorododecanoic acid (0.5 g) was added to the resulting solution to react at room temperature for 3 days, and then dried.

The modified polymer thus obtained was dissolved in tetrahydrofuran to give a solution. The resulting solution was applied on a polyurethane sheet. The surface properties and blood compatibility of the polyurethane sheet thus coated were equivalent to those obtained in Example 1.

EXAMPLE 4

The same procedures as described in Example 3 were repeated, except that perfluoropropionic acid was used in place of perfluorododecanoic acid and Biomer (available from Ethicon Corp. USA) was used as the polyurethane. The surface property of the resulting modified polyurethane was similar to that obtained in Example 1.

COMPARATIVE EXAMPLE 1

Polyurethane was treated in the same manner as in Example 1, except that a hydrophilic polymer of polyethyleneoxide (PEO, M.W.: 200) was used in place of perfluorodecanoic acid and stannous octoate was used as a catalyst.

The advancing and the receding contact angles of the polyurethane thus treated were 30° and 20°, respectively, which indicate a significant enhancement in hydrophilicity. The amount of platelets that adhered was small, but the occlusion time of the polyurethane tube measured by a rabbit arterio-arterial shunt method was 120 min. which was shorter than that of Example 1.

Based on the above results, it could be confirmed that the blood compatibility of the polyurethane was enhanced by grafting an extremely hydrophobic fluorine-containing compound to polyurethanes to a greater degree than that obtained by grafting a hydrophic PEO to the polyurethanes.

COMPARATIVE EXAMPLE 2

Polyurethane was treated in the same manner as in Example 1, except that an aliphatic hydrocarbon such as dodecandiol was used instead of perfluorodecanoic acid, and that dibutyl tin diraurate was used as a catalyst.

The advancing and the receding contact angles of polyurethane having relatively low hydrophobic dodecylalkyl chains were 66° and 46°, respectively, which were medium values between those of hydrophobic perfluorodecanoic acid and those of hydrophilic polyethyleneoxide. The adhesion degree of platelets was lower than that of untreated polyurethanes, but was higher than that of modified hydrophobic or hydrophilic polyurethanes. The occlusion time measured by a rabbit arterio-arterial shunt method was 70 min.

Based on the above results, it could be confirmed that the blood compatibility of the modified polyurethane having low hydrophobic aliphatic dodecylalkyl grafted was inferior to that of the modified polyurethane with an extremely hydrophobic fluorine-containing compound.

EXAMPLE 5

The same polyurethane sheet as used in Example 1 was placed in toluene (60 ml). After adding sodium hydride (0.1 g), the resulting mixture was reacted at 0°–5° C. for 1 hr. under nitrogen atmosphere. To the resulting mixture was added perfluorooctyl iodide (1 g) to react for 1 hr. under the same condition. The resultant was washed with toluene and methanol, in turn, and then dried.

The advancing and the receding contact angles of the surface-modified polyurethane so treated were 108° and 50°, respectively. This indicates that the hydrophobicity of the modified polyurethane is highly enhanced. The adhesion degree of platelets was significantly lowered as compared to the untreated sheet.

In addition, the occlusion time of a polyurethane tube measured by a rabbit ex vivo arterio-arterial shunt method was 125 min., which was a highly extended value as compared to that of 50 min. for the untreated polyurethane tube.

Based on the above results, it was confirmed that the blood compatibility of polyurethane was highly enhanced through modification according to the present invention.

EXAMPLE 6

Polyurethane was treated in the same manner as in Example 5, except that perfluoroethyl iodide was used instead of perfluorooctyl iodide.

The advancing and the receding contact angles of the resultant polyurethane were significantly increased as in Example 5.

EXAMPLE 7

Polyurethane (5 g) was dissolved in dimethylformamide (95 ml) to give a solution. The resultant solution was reacted with sodium hydride (0.1 g) and perfluorododecyl iodide (1 g), in turn, in the same manner as in Example 5. The resultant product was precipitated from an excess amount of methanol, followed by separation and drying.

The modified polymer obtained was dissolved in tetrahydrofuran to give a 2% solution. The resulting solution was coated on polyurethane sheets and tubes, respectively. The contact angles, the adhesion degree of platelets and the occlusion time of the sheets and the tubes thus coated were measured. The sheets and the tubes showed the surface properties and blood compatibilities equivalent to those of Example 5.

As can be seen from the above examples and comparative examples, the fluorine-containing compound-grafted polyurethane polymers according to the invention exhibited superior blood compatibility, attributing to their hydrophobic property, inertness, water-repelling property and very low free surface energy intrinsic to the fluorine-containing compounds used. On the contrary, untreated polyurethanes or low hydrophobic aliphatic alkyl-grafted polyurethanes showed inferior blood compatibility. This substantiates the superior effects of the grafted fluorine-containing compounds according to the present invention.

What is claimed is:

1. A process for the preparation of modified polymeric mateirals which comprises reacting a polymeric substrate selected from the group consisting of polyurethane and copolymers thereof directly with a derivative of a fluorine-containing compound selected from the group consisting of saturated $C_1$–C aliphatic perfluorocarbons having a halogen substituent at one terminal in the presence of a strong base.

2. The process of claim 1, wherein the strong base is selected from the group consisting of sodium and potassium hydride, sodium and potassium ethoxide, and sodium and potassium butylate.

3. A modified polymeric material with improved blood compatibility produced by the process of claim 1.

4. The modified polymeric material of claim 3, wherein the material is useful as the materials for artificial hearts, artificial blood vessels, artificial heart valves, artificial blood oxygenators, artificial kidneys or blood vessel catheters.

* * * * *

UNITED STATES PATENT AND TRADEMARK OFFICE
CERTIFICATE OF CORRECTION

PATENT NO. : 5,242,995
DATED      : September 7, 1993
INVENTOR(S) : Young H. Kim, et al It is certified that error appears in the above-indentified patent and that said Letters Patent is hereby corrected as shown below:

Column 1, line 28, "I984" should read --1984--.

Column 4, line 26, "a" should read --as--.

Column 6, line 4, "perflurodecanoic" should read
    --perfluorodecanoic--;
        line 31, after "Example", insert --1--.

Column 7, line 19, "diraurate" should read --dilaurate--.

Column 8, line 46, "$C_1$-C" should read --$C_1$-$C_{12}$--.

Signed and Sealed this

Fifth Day of July, 1994

*Attest:*

BRUCE LEHMAN

*Attesting Officer*    *Commissioner of Patents and Trademarks*